US012121692B2

(12) United States Patent
Ganapathy et al.

(10) Patent No.: US 12,121,692 B2
(45) Date of Patent: Oct. 22, 2024

(54) CATHETER VENT ASSEMBLY AND RELATED SYSTEMS AND METHODS

(71) Applicant: Becton, Dickinson and Company, Franklin Lakes, NJ (US)

(72) Inventors: Manicavasagam Ganapathy, Hosur (IN); Karthik Bhaskar, Coimbatore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 588 days.

(21) Appl. No.: 17/328,792

(22) Filed: May 24, 2021

(65) Prior Publication Data

US 2021/0386989 A1     Dec. 16, 2021

Related U.S. Application Data

(60) Provisional application No. 63/038,548, filed on Jun. 12, 2020.

(51) Int. Cl.
| | |
|---|---|
| *A61M 39/26* | (2006.01) |
| *A61M 5/14* | (2006.01) |
| *A61M 25/06* | (2006.01) |
| *A61M 39/10* | (2006.01) |

(52) U.S. Cl.
CPC .............. *A61M 39/26* (2013.01); *A61M 5/14* (2013.01); *A61M 25/06* (2013.01); *A61M 39/10* (2013.01); *A61M 2005/1402* (2013.01); *A61M 2039/1038* (2013.01); *A61M 2039/1077* (2013.01); *A61M 2039/266* (2013.01)

(58) Field of Classification Search
CPC .. A61M 2039/1038; A61M 2039/1033; A61M 39/26; A61M 2039/261
See application file for complete search history.

(56) References Cited

U.S. PATENT DOCUMENTS

| | | | |
|---|---|---|---|
| 2004/0138626 A1* | 7/2004 | Cote, Sr. ............... | A61M 39/26 604/249 |
| 2020/0009366 A1 | 1/2020 | Abitabilo et al. | |
| 2020/0046948 A1 | 2/2020 | Burkholz et al. | |

FOREIGN PATENT DOCUMENTS

EP          3099374          12/2016

* cited by examiner

*Primary Examiner* — Courtney B Frederickson
(74) *Attorney, Agent, or Firm* — Kirton McConkie; Whitney Blair; Erik Ence

(57) ABSTRACT

A catheter system may include a needleless connector, which may include a distal end, a proximal end, and a valve disposed between the distal end of the needleless connector and the proximal end of the needleless connector. The catheter system may include a vent assembly, which may include a proximal component and a distal component. The proximal component may include a male luer adapter, which may include a male luer. The distal component may include a distal end coupled to the proximal end of the needleless connector, and a proximal end coupled to the male luer adapter. In response to movement of the proximal component from a proximal position to a distal position with respect to the distal component, the male luer of the male luer adapter may open the valve to vent air inside the catheter system.

4 Claims, 9 Drawing Sheets

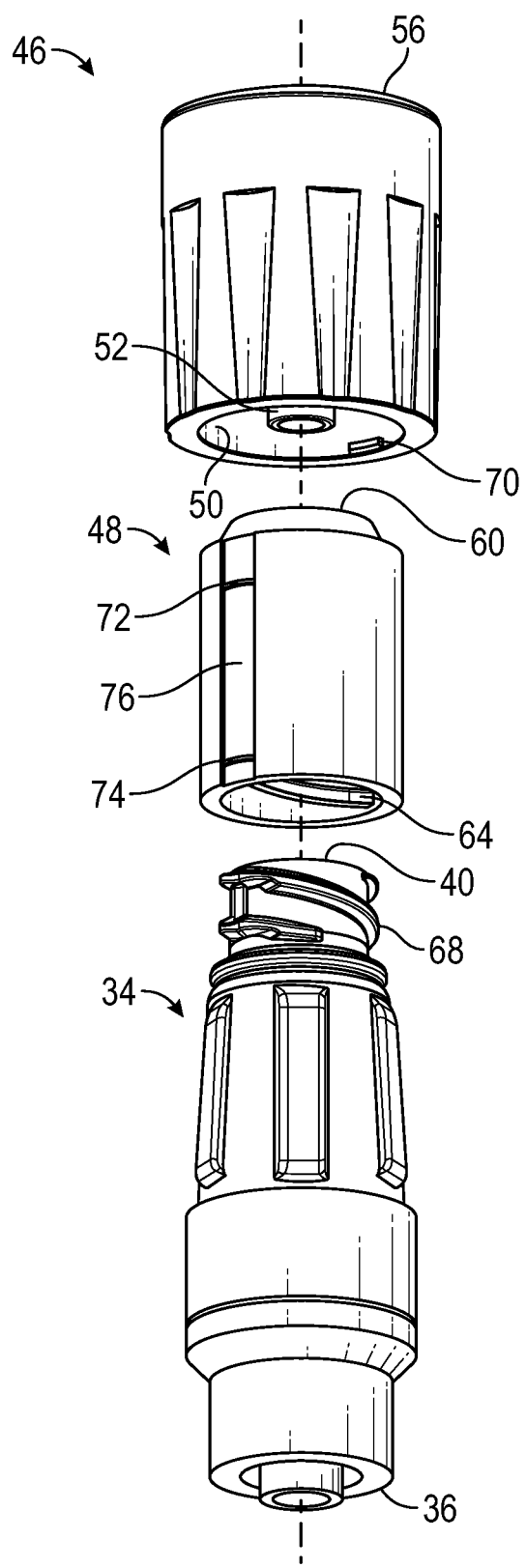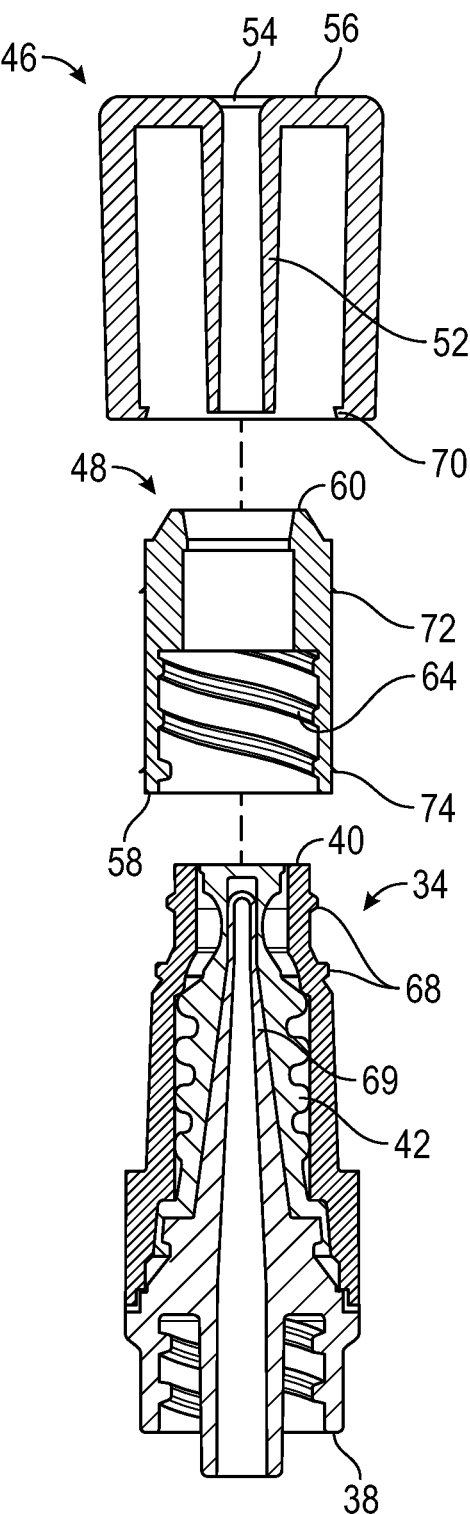
FIG. 4A
FIG. 4B

CATHETER VENT ASSEMBLY AND RELATED SYSTEMS AND METHODS

RELATED APPLICATIONS

This application claims benefit of U.S. Provisional Patent Application No. 63/038,548, filed on Jun. 12, 2020, entitled CATHETER VENT ASSEMBLY AND RELATED SYSTEMS AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and the introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion. The PIVC assembly may be coupled with an extension set, which may allow coupling of an infusion or blood withdrawal device at a location removed from an insertion site of the PIVC.

In some instances, catheters that are used for fluid infusion may be primed prior to insertion into vasculature of the patient to remove air. If air bubbles are allowed to enter vasculature of the patient, an embolism may form, which may cause serious injury to the patient.

The subject matter claimed herein is not limited to embodiments that solve any disadvantages or that operate only in environments such as those described above. Rather, this background is only provided to illustrate one example technology area where some implementations described herein may be practiced.

SUMMARY

In some embodiments, a catheter system may include a catheter assembly and a needle assembly coupled to the catheter assembly. In some embodiments, the needle assembly may include a needle hub and an introducer needle. In some embodiments, a proximal end of the introducer needle may be secured within the needle hub.

In some embodiments, the catheter assembly may include a catheter adapter, which may include a distal end and a proximal end. In some embodiments, the catheter adapter may include a side port disposed between the distal end of the catheter adapter and the proximal end of the catheter adapter. In some embodiments, the catheter assembly may include an extension tube extending from the side port and/or integrated within the side port. In some embodiments, an adapter, such as, for example, a Y-adapter or a T-adapter, may be coupled to the extension tube.

In some embodiments, the catheter assembly may include a catheter, which may extend from the distal end of the catheter adapter and may be secured within the catheter adapter. In some embodiments, the catheter may include a peripheral intravenous catheter (PIVC), a midline catheter, or a peripherally-inserted central catheter.

In some embodiments, the introducer needle may extend through the catheter. In some embodiments, in response to the introducer needle and/or the catheter being inserted into vasculature of a patient, the introducer needle may be proximally withdrawn from the catheter and removed from the catheter assembly. In some embodiments, the catheter may remain within the vasculature of the patient for blood draw and/or fluid infusion.

In some embodiments, the catheter system may include a needleless connector, which may include a distal end, a proximal end, and a valve disposed between the distal end of the needleless connector and the proximal end of the needleless connector. In some embodiments, the distal end of the needleless connector may be coupled to the catheter assembly. In some embodiments, the distal end of the needleless connector may be coupled to the adapter.

In some embodiments, the catheter system may include a vent assembly, which may include a proximal component and a distal component. In some embodiments, the proximal component may include a male luer adapter, which may include a male luer. In some embodiments, the distal component may include a distal end, which may be coupled to the proximal end of the needleless connector. In some embodiments, the distal component may include a proximal end coupled to the male luer adapter. In some embodiments, in response to movement of the proximal component from a proximal position to a distal position with respect to the distal component, the male luer of the male luer adapter may open the valve.

In some embodiments, the male luer adapter may include a first set of threads. In some embodiments, the distal end of the distal component may include a second set of threads. In some embodiments, the first set of threads may be disposed in a different direction than the second set of threads. For example, the first set of threads may be left-handed threads, and the second set of threads may be right-handed threads. Thus, in response to movement of the proximal component from the proximal position to the distal position by threading the proximal component further onto the distal component, a likelihood of unthreading the distal component from the needleless connector may be reduced.

In some embodiments, an outer surface of the distal component may include a third set of threads. In some embodiments, the third set of threads may be a same direction as the first set of threads such that the proximal component and the distal component may be threaded together. For example, the third set of threads may be left-handed.

In some embodiments, an outer surface of the needleless connector may include a fourth set of threads. In some embodiments, the fourth set of threads may be a same direction as the second set of threads such that the needleless connector and the distal component may be threaded together. For example, the fourth set of threads may be right-handed.

In some embodiments, an inner surface of the proximal component may include a first protrusion. In some embodiments, an outer surface of the distal component may include a second protrusion and a third protrusion proximal to the second protrusion. In some embodiments, in response to movement of the proximal component from the proximal position to the distal position, the first protrusion may move proximal to the third protrusion. In some embodiments, in response to the proximal component being in the distal position, the first protrusion may be proximal to the second protrusion.

In some embodiments, an outer surface of the distal component may include a channel. In some embodiments, the second protrusion and the third protrusion may be disposed within the channel. In some embodiments, in response to movement of the proximal component from the proximal position to the distal position, the first protrusion may move proximally within the channel. Thus, in some embodiments, the channel may provide alignment of the proximal component with respect to the distal component.

In some embodiments, the proximal component may include a male luer, a proximal protrusion extending from the male luer, and a distal protrusion extending from the male luer. In some embodiments, the male luer may extend through the proximal end of the distal component. In some embodiments, an inner surface of the distal component may include another protrusion. In some embodiments, in response to movement of the proximal component from the proximal position to the distal position, the proximal protrusion may move distal to the other protrusion. In some embodiments, in response to the proximal component being in the proximal position, the distal protrusion may be distal to the other protrusion and the proximal protrusion may be proximal to the other protrusion.

In some embodiments, a method may include activating the vent assembly, which may be coupled to the needleless connector. In some embodiments, activating the vent assembly may include moving the proximal component from the proximal position to the distal position, which may open the valve. In some embodiments, the method may include priming the catheter assembly after activating the vent assembly, which may allow removal of air through a pathway extending through the needleless connector, the distal component, and the proximal component. In some embodiments, the method may include inserting the catheter assembly into vasculature of a patient after priming the catheter assembly. In some embodiments, the method may include inserting the catheter assembly into the vasculature of the patient and priming the catheter assembly with blood. In some embodiments, the catheter assembly may be primed with blood in response to inserting the catheter assembly into the vasculature. In some embodiments, after inserting the catheter assembly into the vasculature and priming the catheter assembly with blood, the blood may be flushed back into the vasculature.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4A is an exploded view of another example vent assembly and the needleless connector of FIG. 2A, according to some embodiments;

FIG. 4B is an exploded and cross-sectional view of the vent assembly of FIG. 4A and the needleless connector of FIG. 2A, according to some embodiments;

DESCRIPTION OF EMBODIMENTS

Figure 1:
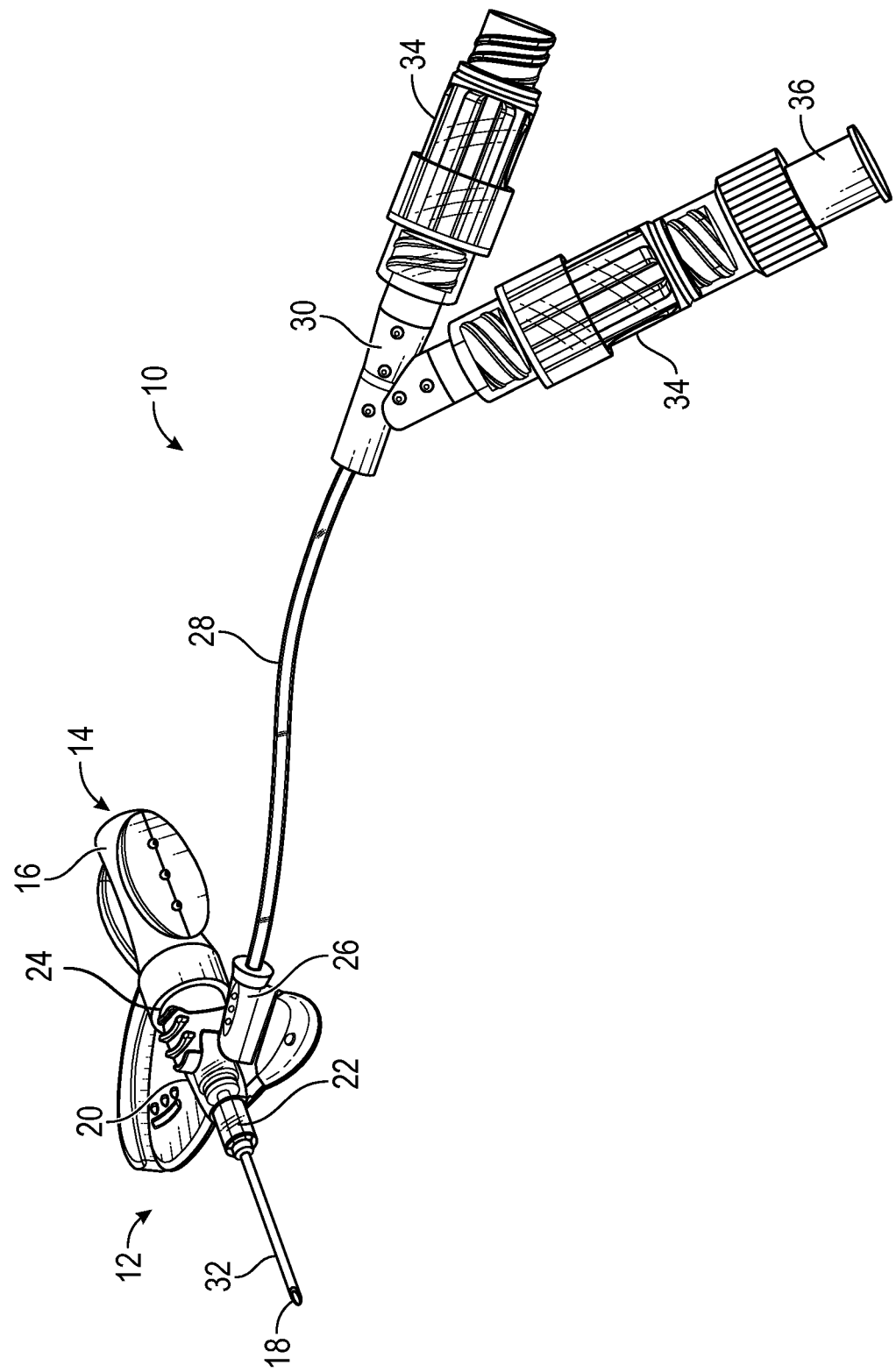
FIG. 1 is an upper perspective view of an example catheter system, according to some embodiments.

Referring now to FIG. 1, in some embodiments, a catheter system 10 may include a catheter assembly 12 and a needle assembly 14 coupled to the catheter assembly 12. In some embodiments, the needle assembly 14 may include a needle hub 16 and an introducer needle 18. In some embodiments, a proximal end of the introducer needle 18 may be secured within the needle hub 16.

In some embodiments, the catheter assembly 12 may include a catheter adapter 20, which may include a distal end 22 and a proximal end 24. In some embodiments, the catheter adapter 20 may include a side port 26 disposed between the distal end 22 of the catheter adapter 20 and the proximal end 24 of the catheter adapter 20. In some embodiments, the catheter assembly 12 may include an extension tube 28 extending from the side port 26 and/or integrated within the side port 26. In some embodiments, an adapter 30, such as, for example, a Y-adapter or a T-adapter, may be coupled to the extension tube 28 at a proximal end of the extension tube 28.

In some embodiments, the catheter assembly 12 may include a catheter 32, which may extend from the distal end 22 of the catheter adapter 20 and may be secured within the catheter adapter 20. In some embodiments, the catheter 32 may include a peripheral intravenous catheter (PIVC), a midline catheter, or a peripherally-inserted central catheter.

In some embodiments, the introducer needle 18 may extend through the catheter 32. In some embodiments, in response to the introducer needle 18 and/or the catheter 32 being inserted into vasculature of a patient, the introducer needle 18 may be proximally withdrawn from the catheter 32 and removed from the catheter assembly 12. In some embodiments, the catheter 32 may remain within the vasculature of the patient for blood draw and/or fluid infusion.

In some embodiments, the catheter system 10 may include one or more needleless connectors 34, which may be coupled to a particular port of the adapter 30. In some embodiments, the needleless connector 34 may include a MAXZERO™ needleless connector available from Becton, Dickinson & Company of Franklin Lakes, New Jersey, or another suitable needleless connector. In some embodiments, a cap 36 may be coupled to a proximal end of a particular needleless connector 34. In some embodiments, the distal end 38 of the needleless connector 34 may be coupled to the adapter 30.

Figure 2A:
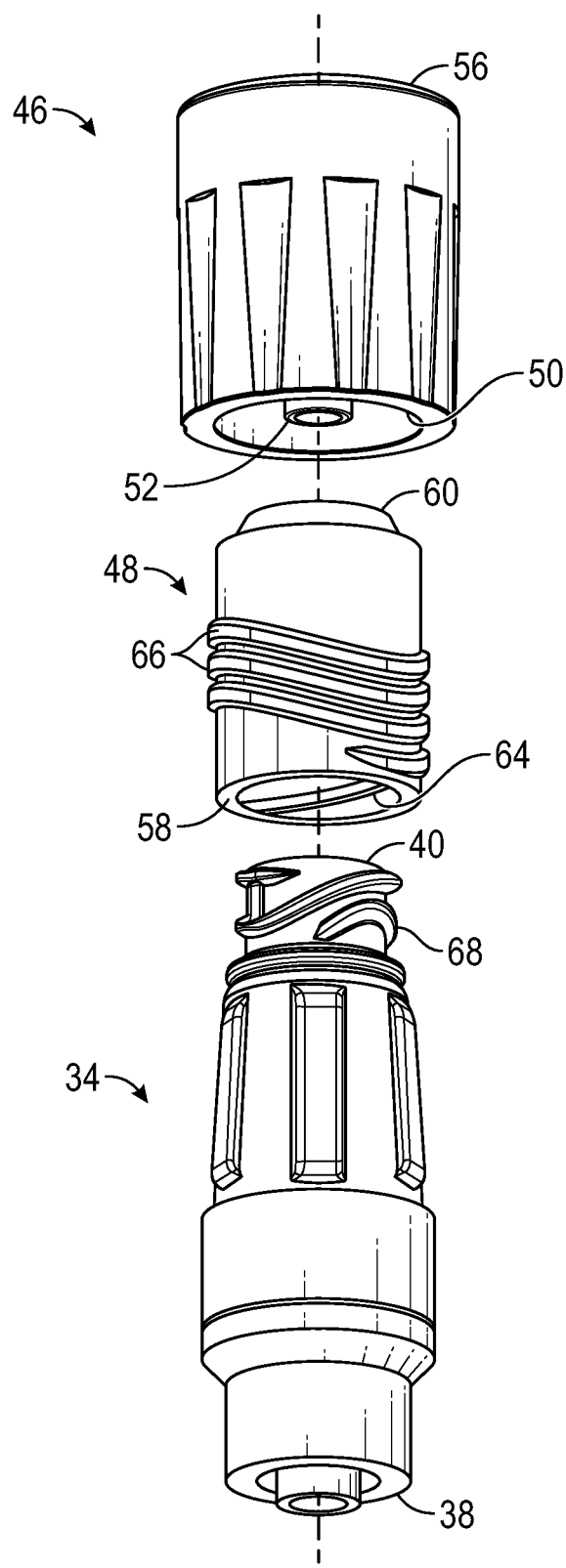
FIG. 2A is an exploded view of an example vent assembly and an example needleless connector, according to some embodiments.
Figure 2B:
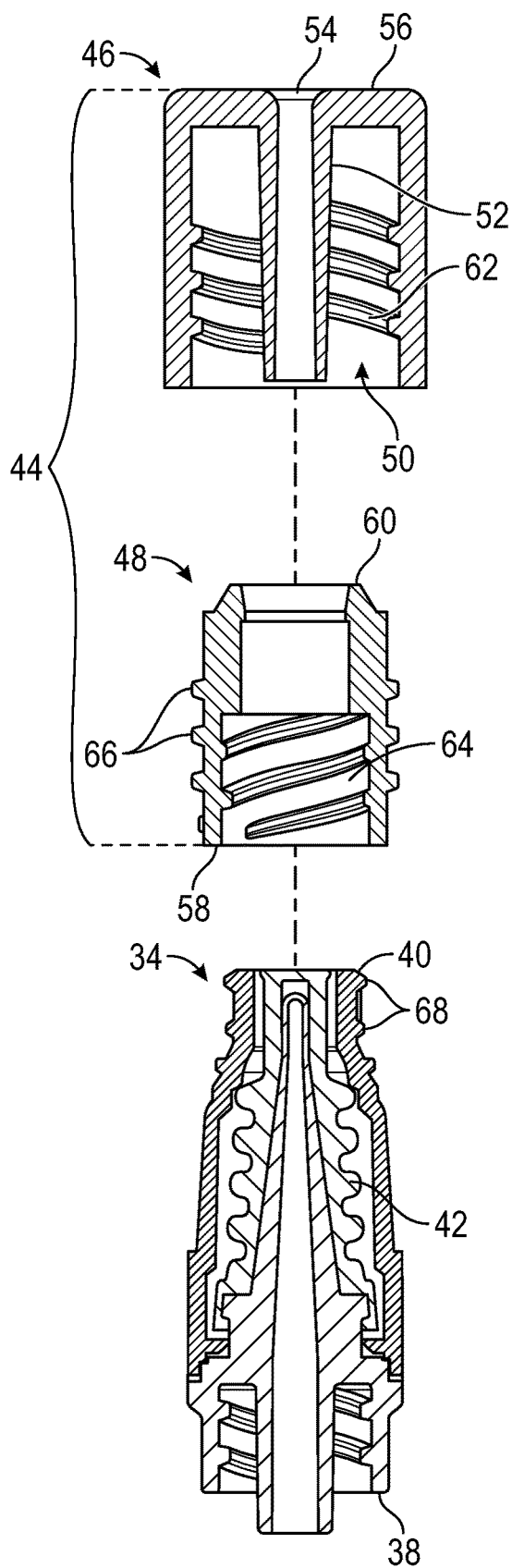
FIG. 2B is an exploded and cross-sectional view of the vent assembly and the needleless connector of FIG. 2A, according to some embodiments.
Figure 2C:
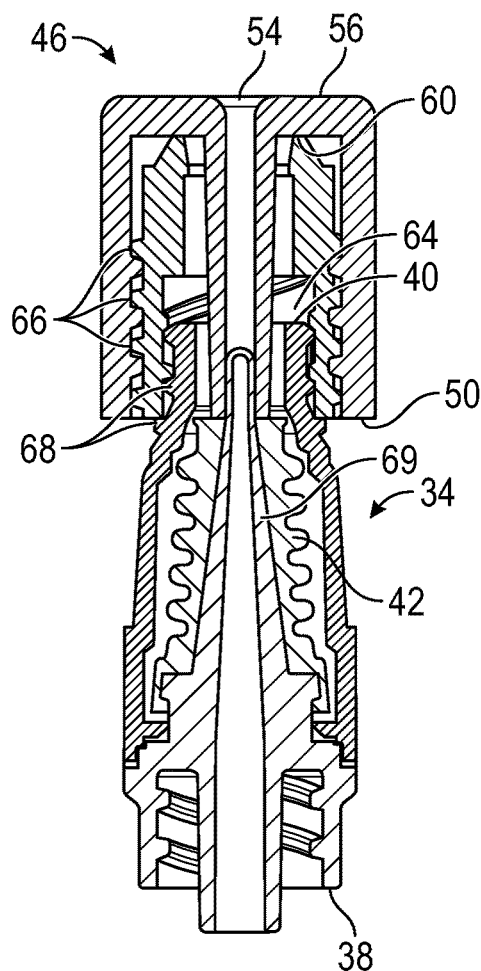
FIG. 2C is a cross-sectional view of the vent assembly coupled to the needleless connector of FIG. 2A, according to some embodiments.

Referring now to FIGS. 2A-2C, in some embodiments, the needleless connector 34 may include a distal end 38, a proximal end 40, and a valve 42 disposed between the distal end 38 of the needleless connector 34 and the proximal end 40 of the needleless connector 34. In some embodiments, the distal end 38 of the needleless connector 34 may be coupled to the catheter assembly 12 (see, for example, FIG. 1).

In some embodiments, the catheter system 10 may include a vent assembly 44, which may include a proximal component 46 and a distal component 48. In some embodiments, the proximal component 46 may include a male luer adapter 50, which may include a male luer 52. In some embodiments, the proximal component 46 may include a vent membrane 54, which may be permeable to air but not liquid. In some embodiments, the vent membrane 54 may be disposed at a proximal end 56 of the proximal component 46. In some embodiments, a fluid pathway may extend through the male luer 52 and may terminate at the vent membrane 54, which may be aligned with the male luer 52.

In some embodiments, the distal component 48 may include a distal end 58, which may be coupled to the proximal end 40 of the needleless connector 34. In some embodiments, the distal component 48 may include a proximal end 60 coupled to the male luer adapter 50. In some embodiments, in response to movement of the proximal component 46 from a proximal position to a distal position with respect to the distal component 48, the male luer 52 of the male luer adapter 50 may open the valve 42, as illustrated, for example, in FIG. 2C.

In some embodiments, the male luer adapter 50 may include a first set of threads 62. In some embodiments, the distal end 58 of the distal component 48 may include a second set of threads 64. In some embodiments, the first set of threads 62 may be disposed in a different direction than the second set of threads 64. For example, the first set of threads 62 may be left-handed threads, and the second set of threads 64 may be right-handed threads. Thus, in response to movement of the proximal component 46 from the proximal position to the distal position by threading the proximal component 46 further onto the distal component 48, a likelihood of the distal component 48 getting stuck to the needleless connector 34 while trying to unthread the vent assembly 44 from the needleless connector 34 may be reduced. Thus, the first set of threads 62 and the second set of threads 64 in different directions may allow easy disengagement of vent assembly 44 from the needleless connector 34.

In some embodiments, an outer surface of the distal component 48 may include a third set of threads 66. In some embodiments, the third set of threads 66 may be a same direction as the first set of threads 62 such that the proximal component 46 and the distal component 48 may be threaded together. For example, the third set of threads 66 may be left-handed.

In some embodiments, an outer surface of the needleless connector 34 may include a fourth set of threads 68. In some embodiments, the fourth set of threads 68 may be a same direction as the second set of threads 64 such that the needleless connector 34 and the distal component 48 may be threaded together. For example, the fourth set of threads 68 may be right-handed.

In some embodiments, a method may include activating the vent assembly 44, which may be coupled to the needleless connector 34. In some embodiments, activating the vent assembly 44 may include moving the proximal component 46 from the proximal position to the distal position, which may open the valve 42. In some embodiments, the valve 42 may include an accordion valve or any other suitable type of valve. In some embodiments, a blunt cannula 69 may extend through the valve 42 and may include one or more flow holes, such that air may be removed through a pathway extending through the needleless connector 34, the distal component 48, and the proximal component 46.

In some embodiments, the method may include priming the catheter assembly 12 after activating the vent assembly 44, which may remove air from the catheter assembly 12 that may be harmful to a patient. In some embodiments, the catheter assembly 12 may be primed with a priming solution such as, for example, saline. In some embodiments, the method may include inserting the catheter assembly 12 into vasculature of the patient after priming the catheter assembly 12.

In some embodiments, the method may include priming the catheter assembly 12 with blood after activating the vent assembly 44, which may remove air from the catheter assembly 12 that may be harmful to a patient. In some embodiments, the catheter assembly 12 may be inserted into the vasculature of the patient and blood may be allowed to fill into the catheter assembly 12 to vent the air through vent assembly 44. In some embodiments, the blood filled in the catheter assembly 12 may be flushed back into the patient's vasculature with a flush solution, for example, saline.

In these embodiments, the catheter assembly 12 and one or more of the following may be filled with blood during priming of the catheter assembly 12: the extension tube 28 (see FIG. 1), the adapter 30 (see FIG. 1), the needleless connector 34, the distal component 48, and the proximal component 46. In some embodiments, after inserting the catheter assembly 12 into the vasculature and priming with blood the catheter assembly and one or more of the extension tube 28 (see FIG. 1), the adapter 30 (see FIG. 1), the needleless connector 34, the distal component 48, and the proximal component 46, the blood may be flushed back into the vasculature with the flush solution. In some embodiments, a flushing device may be coupled to the proximal component 46 to flush the blood back into the vasculature.

Figure 3A:
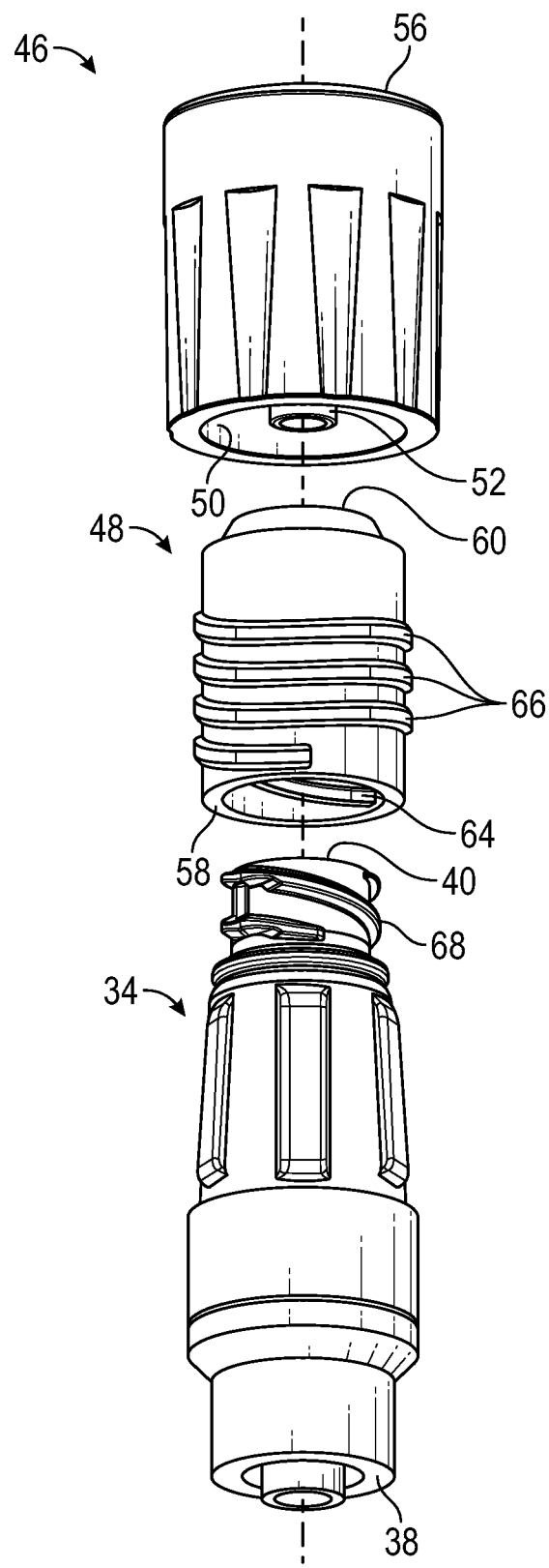
FIG. 3A is an exploded view of another example vent assembly and the needleless connector of FIG. 2A, according to some embodiments.
Figures 3B, 3C:
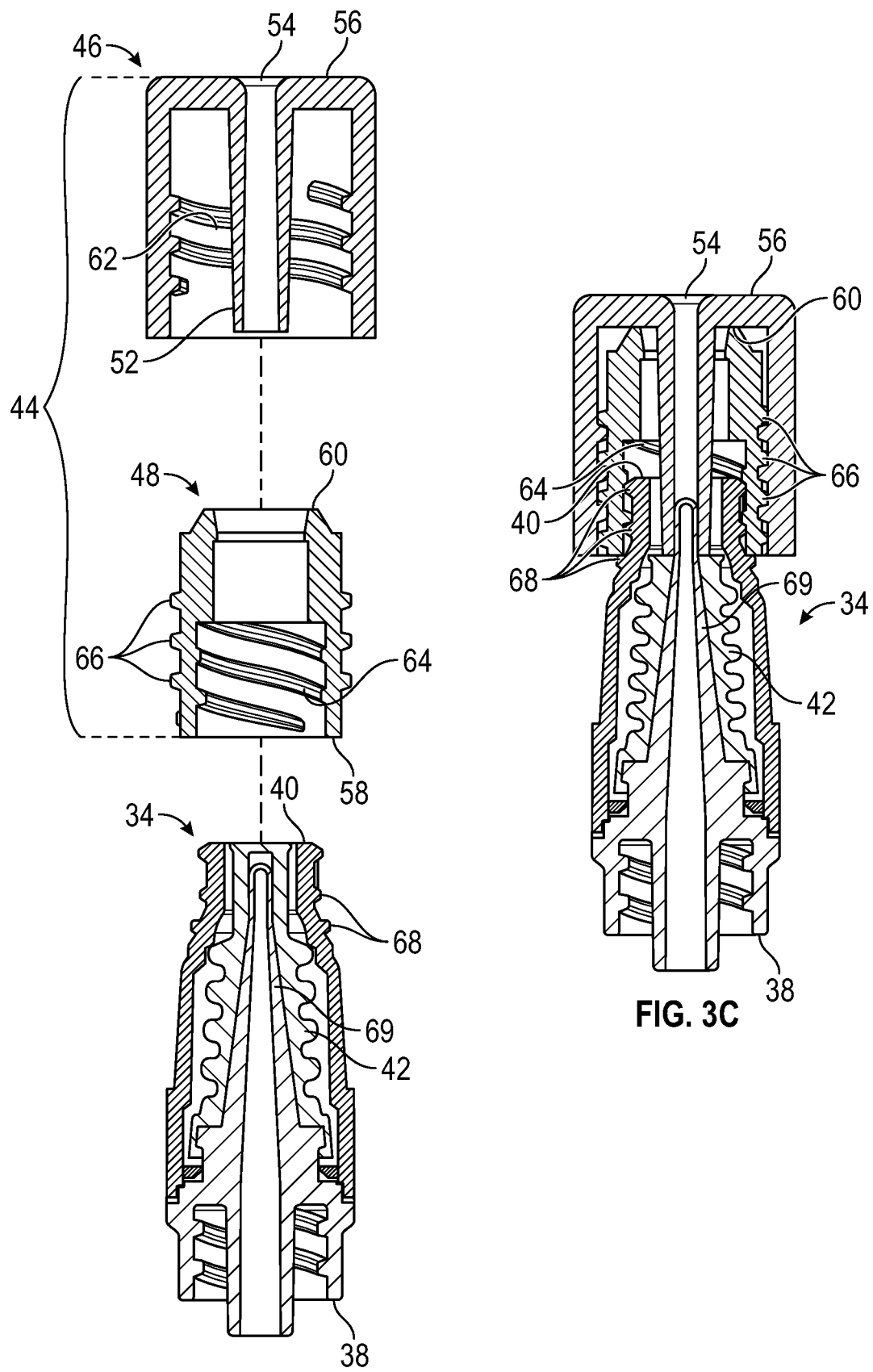
FIG. 3B is an exploded and cross-sectional view of the vent assembly of FIG. 3A and the needleless connector of FIG. 2A, according to some embodiments.
FIG. 3C is a cross-sectional view of the vent assembly of FIG. 3A coupled to the needleless connector of FIG. 2A, according to some embodiments.
Figure 4E:
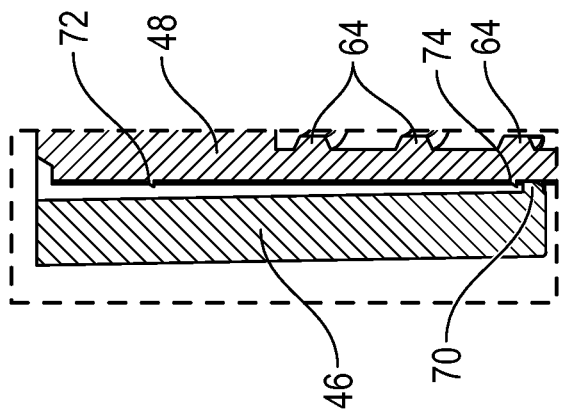
FIG. 4E is a cross-sectional view of a portion of the vent assembly of FIG. 4A, illustrating the proximal component in a distal position, according to some embodiments.
Figure 4D:
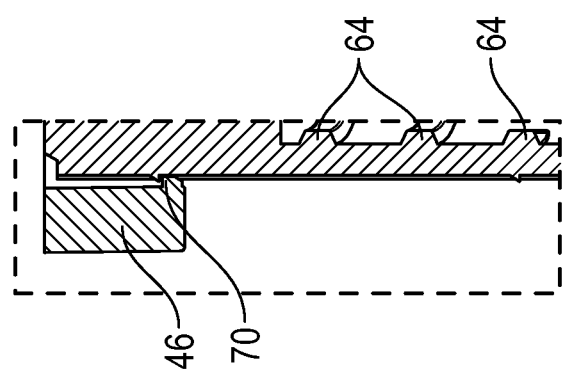
FIG. 4D is a cross-sectional view of a portion of the vent assembly of FIG. 4A, illustrating an example proximal component in a proximal position, according to some embodiments.
Figure 4C:
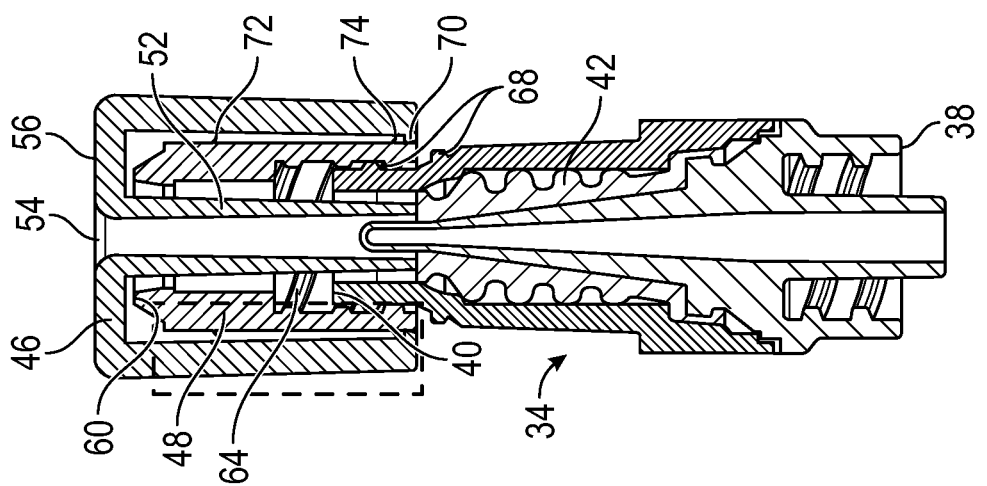
FIG. 4C is a cross-sectional view of the vent assembly of FIG. 4A coupled to the needleless connector of FIG. 2A, according to some embodiments.
Figure 5A:
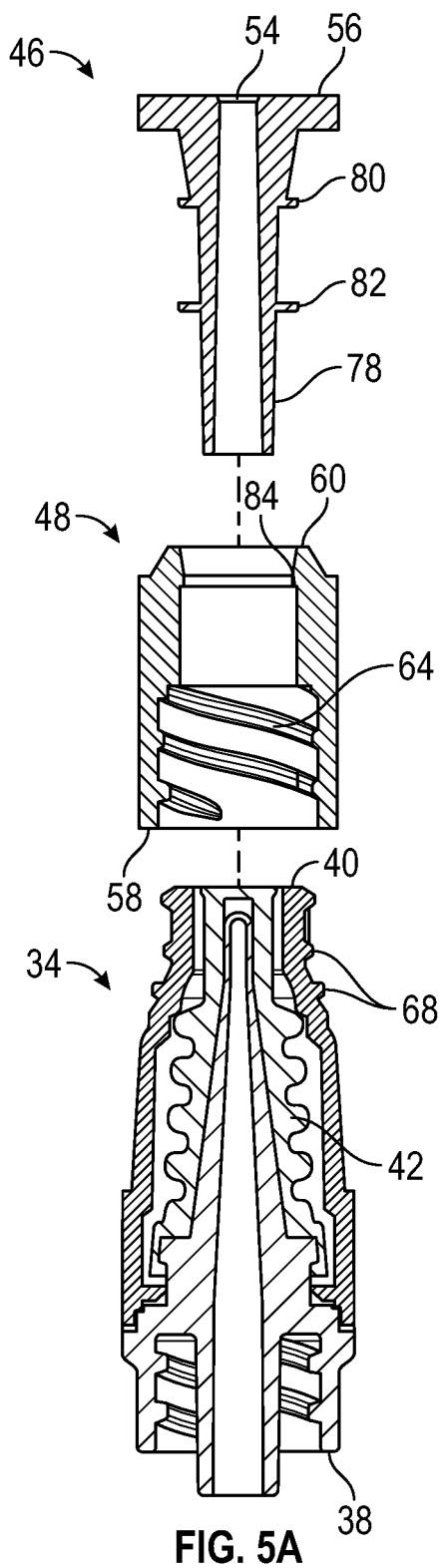
FIG. 5A is an exploded view of another example vent assembly and the needleless connector of FIG. 2A, according to some embodiments.
Figure 5B:
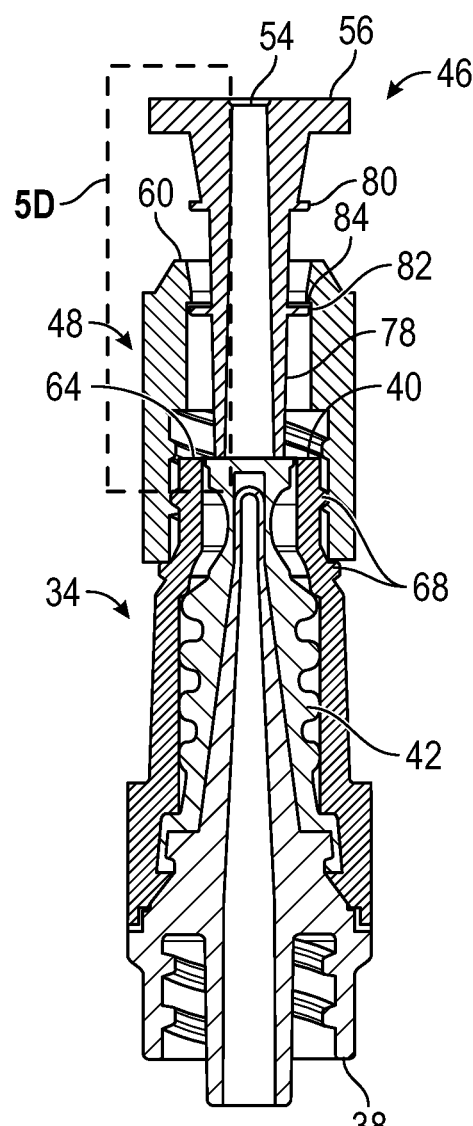
FIG. 5B is a cross-sectional view of the vent assembly of FIG. 5A coupled to the needleless connector of FIG. 2A, illustrating another example proximal component in the proximal position, according to some embodiments.
Figure 5E:
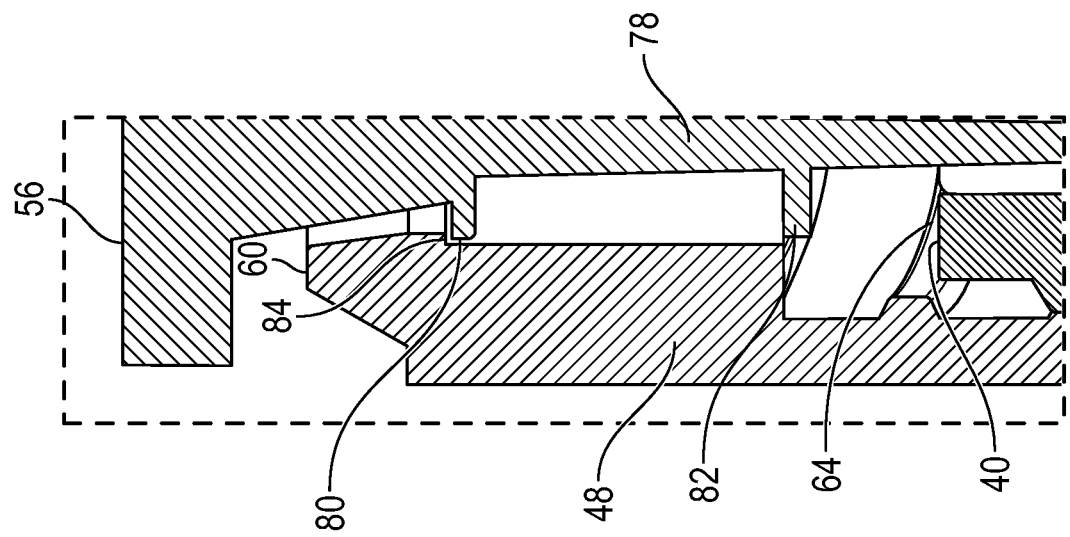
FIG. 5E is a cross-sectional view of a portion of the vent assembly of FIG. 5C, according to some embodiments.
Figure 5D:
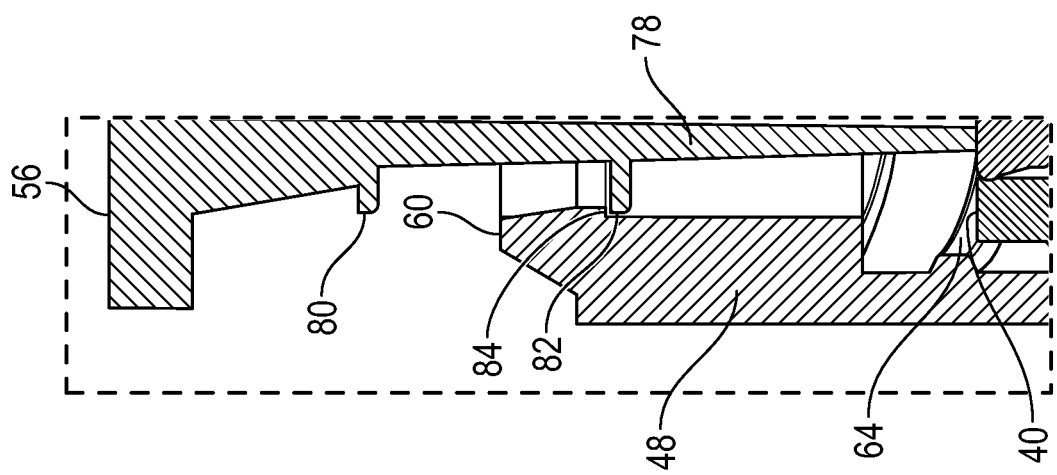
FIG. 5D is a cross-sectional view of a portion of the vent assembly of FIG. 5B, according to some embodiments.
Figure 5C:
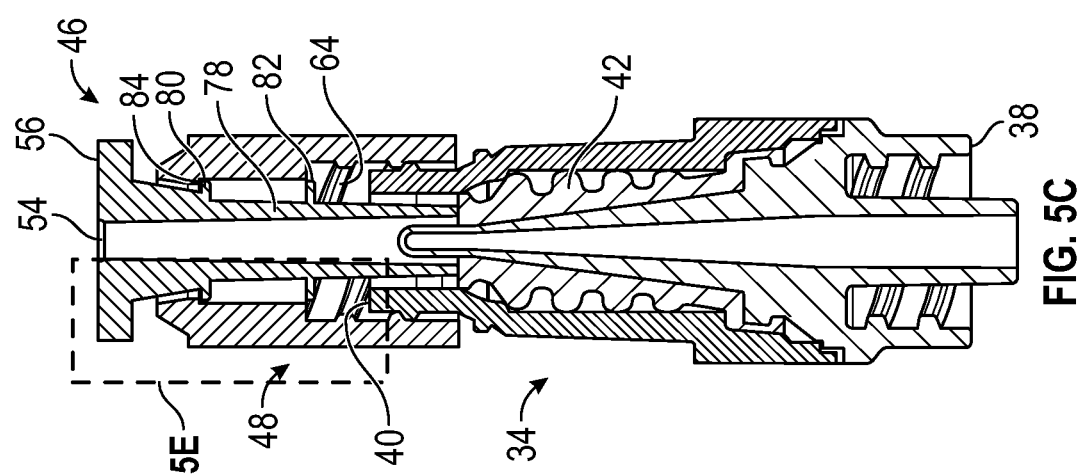
FIG. 5C is a cross-sectional view of the vent assembly of FIG. 5A coupled to the needleless connector of FIG. 2A, illustrating the proximal component in the distal position, according to some embodiments.

Referring now to FIGS. 3A-3B, in some embodiments, the first set of threads 62 may be disposed in a same direction than the second set of threads 64. In some embodiments, the first of threads 62 and the third set of threads 66 may lock permanently/or with a greater force than an unthreading force between the distal component 48 and the needleless connector 34, when the proximal component 46 is in the distal position. Thus, in response to movement of the proximal component 46 from the distal position (in which the valve 42 may be open) to the proximal position by unthreading the proximal component 46 until the disengagement from needleless connector 34, a likelihood of the distal component 48 getting stuck to the needleless connector 34 while trying to unthread the vent assembly 44 from the needleless connector 34 may be reduced.

Referring now to FIGS. 4A-4E, in some embodiments, an inner surface of the proximal component 46 may include a first protrusion 70. In some embodiments, an outer surface of the distal component 48 may include a second protrusion 72 and a third protrusion 74 distal to the second protrusion 72. In some embodiments, in response to movement of the proximal component 46 from the proximal position to the distal position, the first protrusion 70 may move distal to the third protrusion 74. In some embodiments, in response to the proximal component 46 being in the distal position, the first protrusion 70 may be distal to the second protrusion 72 and between the second protrusion 72 and the third protrusion 74. In some embodiments, the proximal component 46 may snap on the distal component 48 in response to the first protrusion 70 being moved distal to the second protrusion 72.

In some embodiments, an outer surface of the distal component 48 may include a channel 76. In some embodiments, the second protrusion 72 and the third protrusion 74 may be disposed within the channel 76. In some embodiments, in response to movement of the proximal component from the proximal position to the distal position, the first protrusion 70 may move distally within the channel 76. Thus, in some embodiments, the channel 76 may provide alignment of the proximal component 46 with respect to the distal component 48.

In some embodiments, one or more of the first protrusion 70, the second protrusion 72, and the third protrusion 74 may be annular. In some embodiments, the proximal component 46 may include at least two of the first protrusions 70. In some embodiments, the distal component 48 may include at least two of the second protrusions 72 and/or at least two of the third protrusions 74. In some embodiments, the distal component 48 may include at least two of the channels 76. In some embodiments, one or more of the following may oppose each other: two of the first protrusions 70, two of the second protrusions 72, two of the third protrusions 74, and two of the channels 76. In some embodiments, the distal component 48 may be monolithically formed as a single unit. In some embodiments, the proximal component 46 may be monolithically formed as a single unit.

Referring now to FIGS. 5A-5E, in some embodiments, the proximal component 46 may include a male luer 78, a proximal protrusion 80 extending from the male luer 78, and a distal protrusion 82 extending from the male luer 78. In some embodiments, the male luer 78 may extend through the proximal end 60 of the distal component 48. In some embodiments, an inner surface of the distal component 48 may include another protrusion 84. In some embodiments, in response to movement of the proximal component from the proximal position to the distal position, the proximal protrusion 80 may move distal to the other protrusion 84. In some embodiments, in response to the proximal component 46 being in the proximal position, the distal protrusion 82 may be distal to the other protrusion 84 and the proximal protrusion 80 may be proximal to the other protrusion 84.

In some embodiments, one or more of the proximal protrusion 80, the distal protrusion 82, and the other protrusion 84 may be annular. In some embodiments, the proximal component 46 may include at least two of the proximal protrusions 80 and/or at least two of the distal protrusions 82. In some embodiments, the distal component 48 may include at least two of the other protrusions 84. In some embodiments, one or more of the following may oppose each other: two of the proximal protrusions 80, two of the distal protrusions 82, and two of the other protrusions 84.

In some embodiments, an outer diameter of the proximal component 46 at the distal protrusion 82 and the proximal protrusion 80 may be greater than an inner diameter of the distal component 48 at the other protrusion 84, such that the distal protrusion 82 and the proximal protrusion 80 may be configured to compress slightly to pass the other protrusion 84. In some embodiments, the distal protrusion 82 and the proximal protrusion 80 may be configured to snap past the other protrusion 84 which may increase difficulty of removing the proximal component 46 from the distal component 48 and/or movement of the proximal component 46 from the distal position (in which the valve 42 may be open) to the proximal position. In some embodiments, the proximal protrusion 80 may contact the other protrusion 84 in response to the proximal component 46 being in the distal position.

In some embodiments, activating a vent assembly, including the distal component 48 and the proximal component 46, coupled to the needleless connector 34, may include moving the proximal component 46 from the proximal position to the distal position. In some embodiments, in response to the moving the proximal component 46 from the proximal position to the distal position, the proximal protrusion may move distal to the other protrusion 84.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter system, comprising:
   a needleless connector, comprising a distal end, a proximal end, and a valve disposed between the distal end of the needleless connector and the proximal end of the needleless connector;
   a vent assembly, comprising:
      a proximal component, comprising a male luer adapter comprising a male luer; and
      a distal component, comprising:
         a distal end coupled to the proximal end of the needleless connector; and
         a proximal end coupled to the male luer adapter,
      wherein the proximal component is movable between a proximal position and a distal position with respect to the distal component, wherein in response to movement of the proximal component from the proximal position to the distal position, the male luer of the male luer adapter opens the valve, wherein the male luer adapter comprises a first set of threads, wherein the distal end of the distal component comprises a second set of threads, wherein the first set of threads is a different direction than the second set of threads.

2. The catheter system of claim 1, wherein the first set of threads is left-handed threads, wherein the second set of threads is right-handed threads.

3. The catheter system of claim 2, wherein an outer surface of the distal component comprises a third set of threads, wherein the third set of threads is left-handed.

4. The catheter system of claim 3, wherein an outer surface of the needleless connector comprises a fourth set of threads, wherein the fourth set of threads is right-handed.

\* \* \* \* \*